US012251261B2

(12) United States Patent
Moal et al.

(10) Patent No.: US 12,251,261 B2
(45) Date of Patent: Mar. 18, 2025

(54) DEVICE FOR ACQUIRING A SEQUENCE OF ULTRASONOGRAMS AND ASSOCIATED METHOD

(71) Applicant: DESKI, Bordeaux (FR)

(72) Inventors: Olivier Moal, Bordeaux (FR); Bertrand Moal, Bordeaux (FR); Emilie Roger, Bordeaux (FR)

(73) Assignee: DESKI, Bordeaux (FR)

( * ) Notice: Subject to any disclaimer, the term of this patent is extended or adjusted under 35 U.S.C. 154(b) by 0 days.

(21) Appl. No.: 18/560,302

(22) PCT Filed: May 24, 2022

(86) PCT No.: PCT/EP2022/064109
§ 371 (c)(1),
(2) Date: Nov. 10, 2023

(87) PCT Pub. No.: WO2022/248500
PCT Pub. Date: Dec. 1, 2022

(65) Prior Publication Data
US 2024/0225589 A1 Jul. 11, 2024

(30) Foreign Application Priority Data

May 28, 2021 (FR) ...................................... 2105597

(51) Int. Cl.
*A61B 8/14* (2006.01)
*A61B 8/00* (2006.01)
(Continued)

(52) U.S. Cl.
CPC ............ *A61B 8/0883* (2013.01); *A61B 8/463* (2013.01); *A61B 8/5269* (2013.01);
(Continued)

(58) Field of Classification Search
CPC ..... A61B 8/0883; A61B 8/5269; A61B 8/463; G06T 2207/10132; G06T 2207/20081;
(Continued)

(56) References Cited

U.S. PATENT DOCUMENTS

2019/0130554 A1* 5/2019 Rothberg .............. G06T 7/0002
2020/0245976 A1 8/2020 Cadieu et al.

OTHER PUBLICATIONS

International Search Report as issued in International Patent Application No. PCT/EP2022/064109, dated Aug. 16, 2022.
(Continued)

*Primary Examiner* — Joel F Brutus
(74) *Attorney, Agent, or Firm* — Pillsbury Winthrop Shaw Pittman LLP (57) ABSTRACT

A device to receive in real time ultrasound images acquired by an ultrasound probe, includes a first calculator for implementing a classifier to classify in real time the received ultrasound images and to associate each image with a class for generating a quality indicator as a function of the associated class, a display for displaying the received ultrasound images and the last generated quality indicator, and a second calculator configured to, when a sequence of a predefined number of received images includes a rate of images associated with a same class greater than a predefined rate, automatically record the sequence of images, and to generate and display, on the display, a time indicator representing a number of remaining images to be received to reach the sequence of a predefined number of received images including a rate of images associated with a same class greater than a predefined rate.

13 Claims, 2 Drawing Sheets

(51) Int. Cl.
  *A61B 8/08* (2006.01)
  *G06T 7/00* (2017.01)
  *G06V 10/764* (2022.01)
  *G06V 10/82* (2022.01)

(52) U.S. Cl.
  CPC .......... *G06T 7/0012* (2013.01); *G06V 10/764* (2022.01); *G06V 10/82* (2022.01); *G06T 2207/10132* (2013.01); *G06T 2207/20081* (2013.01); *G06T 2207/20084* (2013.01); *G06T 2207/30048* (2013.01); *G06T 2207/30168* (2013.01); *G06V 2201/031* (2022.01)

(58) Field of Classification Search
  CPC . G06T 2207/20084; G06T 2207/30048; G06T 2207/30168
  See application file for complete search history.

(56) References Cited

OTHER PUBLICATIONS

Written Opinion of the International Searching Authority as issued in International Patent Application No. PCT/EP2022/064109, dated Aug. 16, 2022.

\* cited by examiner

DEVICE FOR ACQUIRING A SEQUENCE OF ULTRASONOGRAMS AND ASSOCIATED METHOD

CROSS-REFERENCE TO RELATED APPLICATIONS

This application is the U.S. National Stage of PCT/EP2022/064109, filed May 24, 2022, which in turn claims priority to French patent application number 2105597 filed May 28, 2021. The content of these applications are incorporated herein by reference in their entireties.

FIELD OF THE INVENTION

The present invention relates to a device and a method for automating and assisting an operator in taking ultrasound images. Advantageously, the present invention allows the automatic recording of specific shots of the heart, which can subsequently be analyzed by a clinician.

PRIOR ART

Ultrasound imaging, also known as echographic imaging, is a medical imaging technique that uses high-frequency waves to visualize a two-dimensional structure within the body of a living subject. Since ultrasound images are taken in real time, these ultrasound images show the movement of the internal organs in the body as well as the movements of the heart during these beats.

To acquire such images, an ultrasound probe is placed directly on the skin of the subject. A thin layer of gel can be applied to the skin to allow the ultrasound waves to pass through the skin from the probe to the inside of the body of the subject. Ultrasound images are produced by measuring the reflection of ultrasound waves on the organs of the subject. The amplitude of the reflected waves measured, and the time of flight of that wave provide the information needed to reconstruct the ultrasound image.

During an ultrasound examination of the heart, the operator has to know where to place the probe and how to orient it to obtain the desired image. Generally, the desired images from a heart ultrasound are images that allow certain measurements to be made, especially organ or tissue lengths.

In order to increase ultrasound examination capacity, it has been thought to relieve cardiologists from taking images. For example, the images can be taken by an operator who will record the images and then transmit them to a cardiologist who will only have to interpret them. Such an organization thus increases the number of ultrasound examinations by a cardiologist. However, it is then necessary to be certain that the ultrasound images are of sufficient quality to be interpreted by a cardiologist. The operator may have some knowledge of ultrasound, but when he or she will not be carrying out the analysis of the images himself/herself, there is a need for a device for assisting in taking such ultrasound images. Furthermore, the operator does not just need to acquire a single image of sufficient quality, but a sequence of images of sufficient length, for example over a complete beat cycle, for the cardiologist to be able to perform his or her diagnosis and/or analysis.

Software-implemented methods are known to guide the operator in taking ultrasound images of the heart. These methods include assessing the quality of a sequence of images with respect to a particular view and recording such a sequence.

One drawback of these methods is that it remains difficult for the operator to assess when the quality of the image he or she is taking is sufficient. Another drawback of these methods is that it may be difficult to obtain a sufficiently long sequence of images corresponding to the required quality, making it even more difficult for the operator to have his or her shot validated by the software.

There is therefore a need for a new device to make it easier for the operator to take ultrasound images.

The invention therefore aims to provide a device and an associated method allowing operators to acquire ultrasound image sequences of sufficient quality more easily and more quickly.

SUMMARY OF THE INVENTION

According to one aspect, the invention relates to a device for assisting in creating or acquiring a sequence of ultrasound images, preferentially of ultrasound images of the heart, configured to receive in real time ultrasound images acquired by an ultrasound probe connected to said device, and comprising:
  a first calculator, associated with a first memory, to implement a classifier configured to classify in real time the ultrasound images received and associate with each image a class to generate a quality indicator according to said associated class;
  a display for, in real time, displaying the received ultrasound images and for displaying the last generated quality indicator;
  a second calculator, associated with a second memory, and configured to perform the following steps of:
    when a sequence of a predefined number of received images includes a rate of images associated with a same class greater than a predefined rate, automatically recording said sequence of images in a third memory;
    generating and displaying, on the display in real time, a time indicator representing the number of remaining images to be received to reach said sequence of a predefined number of received images comprising a rate of images associated with a same class greater than a predefined rate.

One advantage is to generate a real time image comprising a quality indicator indicating to the operator that the acquired image is of sufficient quality and the time indicator indicating to the operator that the acquisition of a video sequence is in progress as well as the remaining time during which he or she has to maintain a position in which the acquired images are still of sufficient quality. The sequences thus recorded allow the generation of video sequences that the cardiologist can use to establish his or her diagnosis.

According to one embodiment, the first, second and third memories are a same memory. According to one embodiment, the first and second memories are a same memory. According to one embodiment, the first and third memories are a same memory. According to one embodiment, the second and third memories are a same memory. Thus, in the present application, a memory is indifferently referred to as a physical device for storing data or an available memory space of a physical device.

According to one embodiment, the first calculator and/or the second calculator is/are locally included in the device of the invention. According to another mode, the first calculator and/or the second calculator is included in a remote equipment such as a data server. In the latter case, the device of the invention is meant as a system including several pieces of equipment.

In one embodiment, the classifier is configured to classify an image among a plurality of classes, each representing a particular view of the heart organ, and at least one class representing a view of insufficient quality. The advantage is that it is possible to detect both a particular view of the heart and images that would not be usable by the cardiologist to make a diagnosis.

In one embodiment, the classifier is implemented by means of a learning function configured from supervised machine learning.

In one embodiment, the classifier is implemented by means of a neural network trained on a series of labelled ultrasound images of the heart. The advantage of such a classifier is that it allows reliable classification of ultrasound images from training from labelled images.

According to one example, the neural network is a convolutive neural network, known as CNN or Convet.

According to one embodiment, the configuration of the neural network CNN may comprise:
Convolutions or neural network layers comprising a plurality of multiplications of matrices comprising weighting coefficients obtained from a learning method;
non-linear operations.

According to one embodiment, the configuration of the neural network CNN comprises as input(s) images acquired or received or stored in a memory.

The neural network CNN may comprise convolutions in its first layers and then fully connected neuron layers at the end of the model. In the latter case, these are neurons connected to all the neurons in the previous layer and connected to all those in the next layer.

The convolution layers may comprise a scan of an input matrix producing a series of matrix calculations. The other layers of the neural network typically comprise matrix calculations on the size of the input matrix.

In one example, each convolution comprises a matrix product between an input matrix and a weight matrix and the inclusion of an additional bias.

The application of successive layer processing within the neural network CNN comprises the application of a series of matrix multiplications which are followed by a non-linear function to produce an output of said layer. The succession of these operations defines the depth of the neural network.

According to one example embodiment, the neural network is a multilayer perceptron, known as MLP. According to an example, the neural network may be an MLP-equivalent network.

In one embodiment, said labels including characteristic information of a shot of an image of an organ having a characteristic angle of view and/or size; an image quality; the presence of a portion of an image of the heart and/or the presence of a measurable anatomical shape contour.

In one embodiment, the displayed quality indicator comprises a colored indicator whose color depends on the class associated with the last classified image. In one embodiment, a color is associated with ultrasound images classified as being of insufficient quality. The advantage is to allow the operator to quickly visualize whether the image he or she is acquiring is of sufficient quality.

In one embodiment, the quality indicator is a function of a confidence value of the classification of the last classified image, generated by the classification of said ultrasound image. In one embodiment, at least one of the dimensions of the displayed colored indicator depends on said confidence value. An advantage is to allow the operator to visualize, when the image he or she is acquiring is of good quality, whether a movement of the probe improves the quality or brings the image closer to an image of insufficient quality.

In one embodiment, the displayed time indicator comprises a gauge whose filling depends on the value of the time indicator. Advantageously, the operator visualizes the remaining time during which he or she has to maintain a sufficient acquisition quality for the validation or automatic recording of the sequence.

According to another aspect, the invention relates to a system comprising a device according to the invention and an ultrasound probe. The ultrasound probe is preferably capable of being connected to said device so as to transmit the ultrasound images acquired by the probe to the device.

According to another aspect, the invention relates to a method for assisting in generating a sequence of ultrasound images, preferentially a computer-implemented sequence of ultrasound images of the heart.

Said method comprises:
continuously receiving and displaying ultrasound images, preferentially ultrasound images of the heart from an ultrasound probe;
classifying (200) the received ultrasound images in real time, and associating each image with a class; and
generating and displaying a quality indicator as a function of said class associated with the classified ultrasound image;
when a sequence of a predefined number of received images includes a rate of images associated with a same class greater than a predefined rate, automatically recording said sequence of images in a memory;
generating and displaying in real time a time indicator representing the number of remaining images to be received in order to reach said sequence of a predefined number of received images comprising a rate of images associated with a same class greater than a predefined rate.

In one embodiment, the method further comprises selecting a first class representing a particular first view of the heart, said selection automatically generating:
displaying a first pre-recorded image corresponding to an image of the first ultrasound view of the heart of said first selected class, and/or
displaying a first pre-recorded setpoint of ultrasound probe position on a patient to capture said first particular view of the heart.

Displaying the pre-recorded image and setpoint provides guidance to the operator in searching for the ultrasound images to be obtained.

In one embodiment, the method further comprises, after the automatic recording of said automatic sequence:
automatically selecting a second class representing a second particular view of the heart,
displaying on the display a second pre-recorded ultrasound image corresponding to said second selected class, and/or
displaying on the display a second pre-recorded setpoint of ultrasound probe position on a patient to capture said second particular view of the heart.

In one embodiment, a predefined fraction of the received ultrasound images are classified. Preferably, said predefined fraction is parameterizable or controllable by a user interface. This selection of the rate of received images to be classified makes it possible to always classify the received images in real time, especially when the speed of acquisition of ultrasound images is greater than the speed of classification of these images. In another embodiment, the classification is performed with the last ultrasound image received by the receiver REC.

In one embodiment, the step of generating a quality indicator further comprises generating and displaying a confidence value representative of the certainty of the classification performed, and optionally wherein the displayed quality indicator comprises a colored indicator whose color depends on the classification of the ultrasound image and at least one dimension of which is a function of the confidence value.

According to another aspect, the invention relates to a device comprising software and hardware means for performing the method according to the invention. The hardware means may comprise a display, a receiver REC, an ultrasound probe, one or more processors or calculators associated with memories, one or more memories for storing sequences of ultrasound images, and/or a transmitter.

According to another aspect, the invention relates to a computer program product comprising instructions that cause the device according to the invention to perform the steps of the method according to the invention. According to an aspect, the invention relates to a computer readable support, on which the computer program according to the invention is recorded.

BRIEF DESCRIPTION OF THE FIGURES

Other characteristics and advantages of the invention will become clearer on reading the following detailed description, in reference to the appended figures, that illustrate.

DETAILED DESCRIPTION

The invention relates to a method 1000 of assisting in generating a sequence of ultrasound images. The invention is particularly advantageous for generating a sequence of ultrasound images of the heart. This is because the heart is in an organ subjected to a cycle.

The cardiac cycle consists of two periods: one during which the heart muscle relaxes and fills with blood, called diastole, followed by a period of vigorous contraction and pumping blood, called systole. After emptying, the heart immediately relaxes and expands to receive another inflow of blood returning from the lungs and other systems in the body, before contracting again to pump blood to the lungs and these systems. A normally functioning heart should be fully expanded before it can pump efficiently again.

In order to analyze possible conditions, it is important for the doctor to obtain a sequence of images (or video) of the entire cardiac cycle. The invention advantageously makes it possible to assist the practitioner in acquiring an image sequence.

However, the invention may also find advantages in the ultrasound acquisition of other organs or an image sequence is desirable, for example in the field of obstetric ultrasound.

Figure 2:
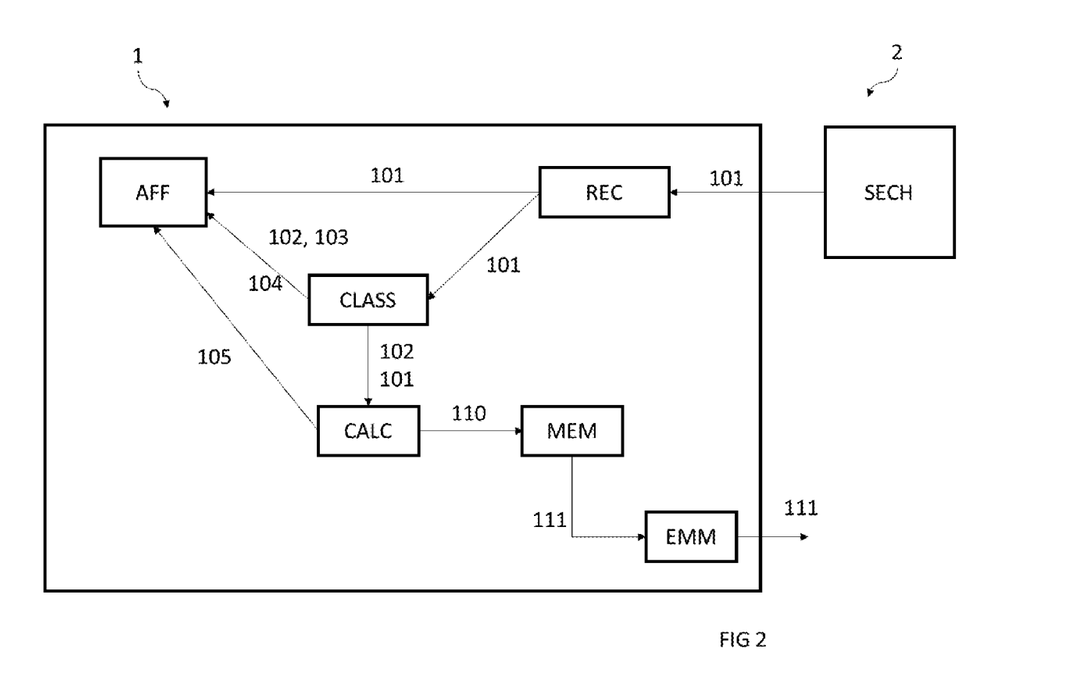
FIG. 2: a schematic view of a device according to an embodiment of the invention.

The invention also relates to an associated device. An example of such device 1 is shown in FIG. 2.

Device 1 may comprise a tablet, a smartphone, a computer, or any other device comprising at least one display and a processor associated with a memory. According to another aspect, the invention also relates to a system 2 comprising a device 1 according to the invention and an ultrasonic probe SECH connected to said device 1.

In one embodiment, the device comprises software and hardware means for implementing the method according to the invention described below. Said device preferably comprises at least one receptor REC, a classifier, and a display.

Reception

The method comprises a step of receiving 100 ultrasound images 11 in real time. Said ultrasound images are received by a receptor REC of the device. In one embodiment, the receiver REC may comprise a buffer memory wherein images received 11 by the receiver REC are temporarily stored prior to transmission.

The received ultrasound images 11 are displayed in real time, preferably on a display AFF of the device. The received ultrasound images can therefore be transmitted to a display for display in real time.

The device includes a display AFF. The display AFF may comprise a screen such as a monitor, a touchscreen tablet or a smartphone.

The display AFF is connected to the receiver REC and/or the classifier CLASS and/or the processor. The display AFF is configured to display in real time the ultrasound images received by the receiver REC. The display AFF advantageously allows the operator to have real-time feedback on the ultrasound images that they are acquiring. The display AFF is configured to show additional indicators or data that will be described later in this description. The display AFF displays an image 1 comprising an ultrasound image received 11 by the receiver REC. Preferably, the ultrasound image displayed is the last ultrasound image received by the receiver REC. The display AFF is thus configured to display in real time the images captured by the ultrasonic probe SECH connected to the device according to the invention.

Classification

The method comprises a step of classifying 200 of the ultrasound images 11 received by the receptor REC in real time. Classification is performed by a classifier CLASS of the device.

The classification of an ultrasound image comprises associating said ultrasound image with a class 14, preferably a class among a predefined class group.

In one embodiment, the classification further comprises generating 300 a quality indicator 13 according to said class associated with the ultrasound image. The quality indicator may be representative of a class or predefined set of classes.

In one embodiment, the step of classifying further comprises generating a confidence value. The confidence value may represent the confidence rate of the classification performed. The confidence value is generated by the classifier CLASS.

The classification step is preferably performed by a classifier CLASS of the device. Classifier means an algorithmic function executed by a processor or a calculator associated with a memory.

The classifier CLASS is configured to receive images received by the receiver REC.

The classifier is configured to classify in real time at least part of the images received by the receiver REC. The classifier is configured to associate a class with an ultrasound image. The classifier generates a quality indicator 13 according to the associated class. The quality indicator 13 is preferably associated with said classified ultrasound image.

Preferably, the image processing means device for processing the images received before providing them to the classifier CLASS. These processing means may comprise image filters or contrast functions.

Preferably, the classifier CLASS is configured to classify an ultrasound image of the heart among a plurality of classes comprising, on the one hand, classes each representing a particular view of the heart and on the other hand, a class representing a view of insufficient quality.

Thus, when an image is classified in a class representing a particular view of the heart, this image is considered to be of sufficient quality to advantageously allow the clinician to perform predefined measurements from these images. Indeed, cardiologists use particular well identified views for their diagnosis.

In one embodiment, each class representing a particular view of the heart represents one of:
The view of a parasternal long axis slice
The view of a parasternal short axis slice
The view of an apical slice
The view of a subcostal slice
The view of a suprasternal slice
The view of a straight paraphernal section Each of these views is well known to cardiologists and is used to visualize different parts of the heart, calculate or measure specific data, and identify certain pathologies.

Each of these views can be characterized by the presence of one or more specific parts of the heart. For example, the view of a parasternal short axis slice is characterized by the presence of the section of the left and right ventricles in the image. From this view, the cardiologist can calculate the shortening fraction and calculate lung pressures.

In one embodiment, the class representing a view of insufficient quality represents ultrasound views of the heart that do not belong to one of the specific views of the other classes or the specific ultrasound views listed above, but whose image quality does not allow the necessary measurements related to that specific view.

In one embodiment, the classifier CLASS is implemented by means of a learning function trained from supervised and/or machine learning. The learning function preferably comprises a neural network. The learning function is preferably trained with a series of labelled ultrasound images of the heart.

In one example, the learning function has been configured from a training comprising submitting a plurality of ultrasound images each associated with a label to the classifier. In one embodiment, the classifier has been trained with ultrasound images of a specific view of the heart of sufficient quality, each image being associated with a label representing said specific view. The classifier has also been trained with ultrasound images of views of the heart other than those listed above or not having a sufficient quality to enable the cardiologist to perform measurements from those images, each of these images being associated with a quality label representing a view of insufficient quality. The labels may also include information characteristic of a shot of an image of an organ having a characteristic angle of view and/or size, an image quality, the presence of a specific portion of an image of the heart, the presence of a measurable anatomical shape contour. Preferably, the labels include the name of the particular view of the heart or a name associated with a poor quality view.

The classifier CLASS may be executed in a processor that is itself associated with a memory. The classifier CLASS may be recorded in a computer readable medium such as a memory associated with said processor.

In one embodiment, the step of classifying an ultrasound image comprises generating a match score for each class. The correspondence score may comprise a probability that the ultrasound image belongs to each class. The method then includes selecting the class with the highest score. Preferably, the confidence value is generated from said correspondence score of the class associated with said ultrasound image.

In an embodiment, the classifier CLASS classifies 100% of the images received in real time.

In an alternative embodiment, the classifier CLASS is configured to classify only one rate of received images. The classifier is then configured to classify a portion of the received ultrasound images in real time. This embodiment is particularly advantageous when the classification speed is less than the image acquisition speed (in images per unit of time).

In one embodiment, the classification of an ultrasound image comprises the classification of the last received ultrasound image. When said image has been classified, the method again takes the last received ultrasound image. As a result, some ultrasound images may not be classified. However, this execution mode advantageously makes it possible to classify ultrasound images in real time, regardless of the speed of the classifier or the frequency of reception of the ultrasound images.

Quality Indicator

The method according to the invention comprises generating and displaying in real time on the display AFF of the quality indicator 13 generated. Preferably, the quality indicator 13 displayed corresponds to the last quality indicator 13 generated.

In one embodiment, this quality indicator 13 is generated by the classifier CLASS. Such a classifier is configured to, upon receiving an ultrasound image of the heart, classify said image into one of the above-mentioned classes. The method then includes generating a quality indicator representative of the classification of that image. Said quality indicator may be associated with said classified ultrasound image.

Alternatively, the quality indicator 13 can be generated by a remote processor connected to the display AFF and receiving information from the classifier.

The display of the quality indicator 13 may comprise the display of a colored indicator the color of which depends on the class associated with the classified ultrasound image. The color of the indicator may be representative of a single class. Preferably, the color of the colored indicator may be of two distinct colors, a first color representative of a group of classes including classes representing a particular view of the heart such as those set out above, and a second color representative of a class representing a view of insufficient quality. Thus, the operator can advantageously visualize more quickly whether the ultrasound image he or she is taking is of sufficient quality or not.

In one embodiment, the classifier is also configured to, upon receiving an ultrasound image of the heart, generate a confidence value. The confidence value may be representative of a level of certainty that the image has been correctly classified. In one embodiment, the quality indicator may comprise said confidence value. Said quality indicator 21 is preferably displayed on the display AFF.

The quality indicator 13 associated with the classified image may include said confidence indicator. In another alternative embodiment, a confidence indicator representative of the confidence value is generated and displayed in real time.

Figure 1:
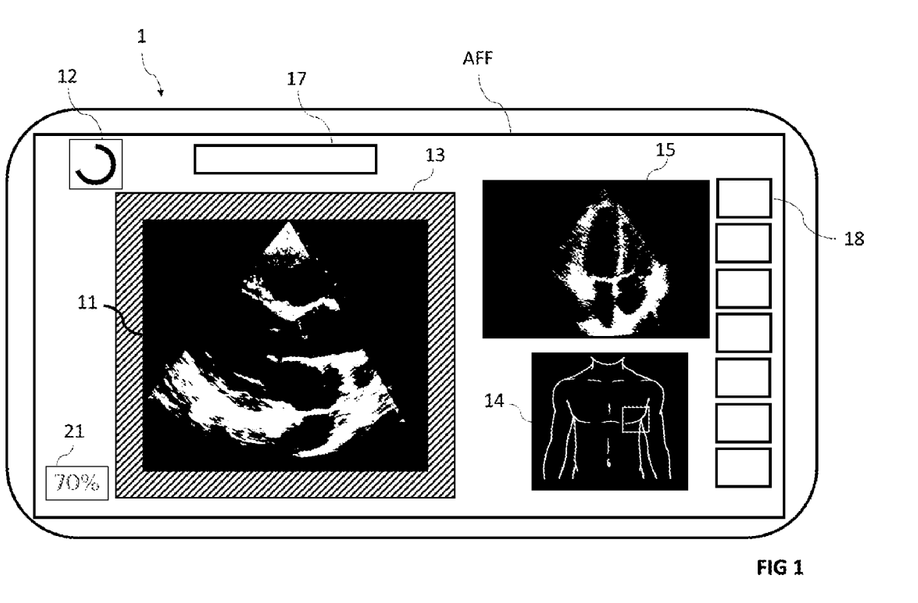
FIG. 1: a schematic view of the image displayed by the display of the device according to a first embodiment of the invention.

In a first example illustrated in FIG. 1, the displayed quality indicator 13 comprises a colored frame, which preferentially extends around the displayed ultrasound image. The operator can then advantageously visualize whether the image he or she is taking is the expected one without having to look away from the image. The confidence indicator can be displayed as a numerical value as illustrated in FIG. 1.

Figure 3:
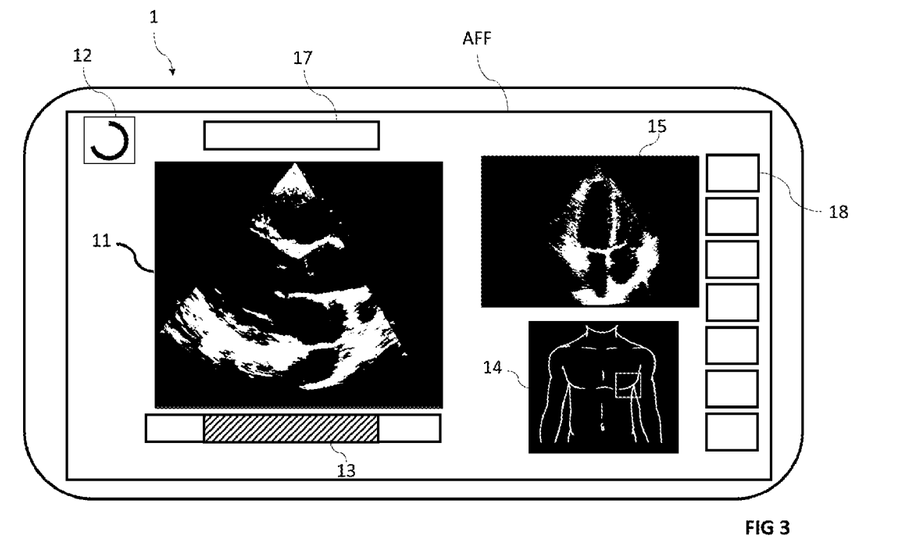
FIG. 3: a schematic view of the image displayed by the display of the device according to a second embodiment of the invention.
Figure 4:
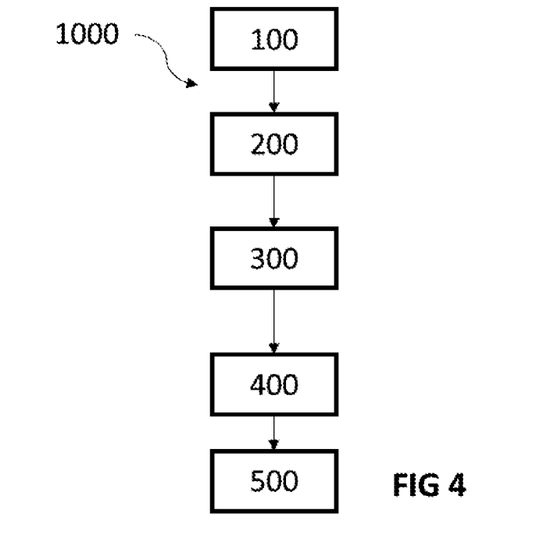
FIG. 4: a flowchart representing the different steps of a method according to one embodiment of the invention.

In a second example illustrated in FIG. 3, the quality indicator 13 comprises a colored indicator. The color of the colored indicator is representative of the classification of the last ultrasound image. At least one of the dimensions of said colored indicator is a function of the confidence value. In the example illustrated in FIG. 3, the quality indicator 13 is a bar whose length varies according to the confidence value and whose color depends on the class associated with the last ultrasound image.

Such an indicator advantageously allows the operator to visualize whether the image he or she is taking is of sufficient quality and also allows him or her to visualize without looking away whether the indicator is degraded or improved as a function of the movement of the ultrasound probe SECH. The purpose of such an indicator is to allow the operator, when moving the probe slightly, to visualize whether this movement increases or decreases the confidence value, and therefore increases or decreases the likelihood of obtaining a validated sequence of images described below.

Sequence

The method comprises automatically recording 400 a sequence 20 of images in a memory MEM. This sequence 20 is automatically recorded when a sequence of a predefined number of received or classified images includes a rate of images associated with a same class 14 greater than a predefined rate. Preferably, said class is a class representing a particular view of the heart.

By "sequence of images" it is meant a series of ultrasound images which follow each other in the chronological order of their acquisition. The term "video sequence" will therefore also be used to refer to such a sequence of images.

Thus, when a sufficiently long video comprises, for example, a majority of ultrasound images classified in the same class representing a particular view of the heart, the video sequence 20 is automatically recorded in a memory. This automatic recording advantageously automatically generates videos of a particular view of the heart that can be analyzed by a cardiologist without validation by the operator.

The predefined number of received or classified images can be understood as a predefined minimum duration, as long as the image acquisition frequency of the ultrasound probe SECH is constant. The advantage of this threshold is to ensure that the video sequence 20 is long enough to be analyzed by a cardiologist. In another embodiment, the predefined number of images may be replaced by a number of received or classified images. The predefined number may be parameterized to correspond to a predefined number of cardiac cycles of the subject's heart.

The rate of images associated with a same class in said video sequence greater than a predefined rate advantageously allows automatic recording despite a negligible number of images not having sufficient quality in said sequence. Indeed, this negligible number of images in a video sequence can come from a classification error, or noise linked to a particular image. This tolerance advantageously consists of a good compromise between the ease of automatic generation of a sequence and the quality of said sequence.

In one embodiment, the predefined rate is at least greater than 50%. In another embodiment, the predefined rate can be set by the operator, for example by a user interface of the device.

In one embodiment, the automatic recording step comprises buffering the continuously received ultrasound images as well as the generated quality indexes associated with said images. In this way, when a video sequence meeting the above criteria is detected, the images belonging to this sequence can be transferred from the buffer memory to another memory, and/or grouped in a same file to generate a video sequence.

For the sake of clarity, the generation and recording of such a sequence will be referred to as the "validation" of such a sequence in the following.

Time Indicator

In one embodiment, the method comprises a step of generating and displaying in real time a time indicator 12.

The displayed time indicator 12 is representative of the number of remaining images to be received or classified in order to reach a sequence of a predefined number of received images comprising a rate of images associated with a same class greater than a predefined rate.

This indicator advantageously allows the operator to visualize the time remaining to validate a video sequence of a particular view of the heart. Advantageously, this indicator allows the operator to visualize the remaining time during which he or she has to maintain an ultrasound image of sufficient quality, said quality being displayed to him/her by the quality indicator 13 and/or the confidence indicator.

The time indicator 12 may comprise a numerical value such as a countdown. The time indicator 12 may comprise a gauge that fills or empties as a function of the time remaining to validate a video sequence.

In one embodiment, the method comprises, when a first image is classified into a class representing a particular view of the heart, automatically generating and displaying the time indicator 12.

With each new classified image, the time indicator 12 is preferentially updated in real time:
  if the number of classified images since the first image includes a rate of images associated with the same class that is greater than the predefined rate, then the time indicator 12 is updated indicating the remaining time or number of remaining images to be received to reach the predefined number of images and the recording of the video sequence 20;
  if the number of classified images since the first image includes a rate of images associated with the same class that is less than the predefined rate, then the time indicator 12 is updated to indicate the failure of the validation, for example by resetting the counter or gauge to zero or by making the displaying of such a counter or gauge disappear.

The method comprises displaying in real time the received ultrasound images, the quality indicator 13, and optionally the time indicator 12. Such displaying is described below with reference to FIG. 2. The image displayed by the display AFF comprises the ultrasound image 11 received in real time or taken in real time by the ultrasound probe SECH, the quality indicator 13 and the time indicator 12.

Program

According to one embodiment, the method according to the invention comprises selecting a first class from among the classes representing a particular view of the heart such as one of the above-mentioned views.

The selection of the first class generates displaying a first pre-recorded ultrasound image 15 of the heart representing such a view on the display AFF. Preferably, the label 17 which may include the name of said particular view is also displayed on the display AFF. Selecting the first class also generates the display of a first setpoint image 14. The first setpoint image 14 is preferably pre-recorded. The setpoint image shows a position and/or orientation setpoint of the ultrasound probe SECH on a patient to obtain said view corresponding to the class selected. The operator is thus advantageously guided and assisted in taking such a view. On the same display AFF, they can view an example of the view that they must take, the position and orientation of the probe to achieve this. Finally, the operator can view in real time whether the view acquired is of sufficiently good quality by the quality indicator 13, and can advantageously view the influence of the movements they perform on the quality of the image acquired thanks to the confidence indicator.

Finally, once the operator has found an image of satisfactory quality, they are assisted in real time by the time indicator 12 representative of the time during which they must hold the probe to acquire images of sufficient quality. The operator is also assured, by visualizing the time indicator 12, that a first sequence 20 is going to be recorded by maintaining its position.

Once the first sequence has been recorded or validated, the method may include automatically selecting a second class from among the classes representing a particular view of the heart such as one of the above-mentioned views. Again, the selection of said second class automatically generates displaying a second pre-recorded target image and displaying a second pre-recorded ultrasound image illustrating an ultrasound view.

According to one embodiment, the method further comprises generating and displaying a progress indicator 18. The progress indicator may represent the number of sequences that have been recorded. For example, the progress indicator is representative of the number of classes representing a particular view of the heart for which a sequence 20 of images has been automatically generated and/or recorded according to the method of the invention.

According to one embodiment, the method comprises displaying the recorded sequence and further comprises a second manual validation by the operator after displaying said sequence.

Device

According to one aspect, the device according to the invention comprises software and hardware means for implementing the method such as described above.

An embodiment of the device according to the invention is now described in reference to FIG. 2.

The device includes a receptor REC. The receiver REC is intended to be connected to an ultrasonic probe SECH in such a way as to receive continuously and in real time ultrasound images 11 acquired by said ultrasonic probe SECH.

The receiver REC can be connected to the ultrasonic probe SECH by a wired or wireless link, for example by a Bluetooth connection or a WI-FI connection or any other data exchange protocol known to those skilled in the art.

The receiver REC may comprise or be associated with one or more memories to temporarily store the images received. The receiver REC is directly or indirectly connected to the display AFF to transmit to the display AFF the ultrasound images acquired 11.

The device further comprises means for implementing a classifier CLASS such as described above. The classifier is configured to receive ultrasound images 11, associate a class 14 with ultrasound images in real time, and generate the quality indicator 13 in real time. The classifier is connected directly or indirectly to the display AFF to transmit the indicators generated to the display AFF.

According to an alternative, the classifier is implemented by remote electronic equipment, such as a remote server. In this case, the device comprises an interface to exchange data with the remote equipment in order to transmit data and retrieve the result of the processed, i.e., classified, data.

Finally, in the present invention, it is understood that when the classification is implemented wholly in part by remote equipment, the device of the invention can be interpreted as being the system comprising on the one hand the local device described in the present application and the remote means making it possible to implement the classification function.

The device further comprises at least one processor or calculator CALC associated with a memory for performing at least part of the steps of the method according to the invention. For example, said processor may be configured to perform the steps of classifying 200, generating the display of the quality indicator 300 and the time indicator 500 and/or automatically recording 300 the sequence 20 of images. Said processor may be connected to the display AFF to transmit the time indicator 12 to the display AFF.

The device 1 may also comprise a plurality of processors, each associated with one or more memories, and configured to perform such steps together. In one embodiment, the processor(s) may be remote and connected to the display via a data network.

The device further comprises a memory for storing or recording sequences generated by the method according to the invention. In one embodiment, the device further comprises a transmitter EMM connected to said memory MEM to transmit said sequences recorded on said memory MEM to a data network.

The display AFF may comprise means to receive the different information 11, 13, 21, 12 received by the different means REC, CLASS, PROC of the device to generate the final image to display.

The invention claimed is:

1. A device for assisting in creating a sequence of ultrasound images of the heart, configured to receive in real time ultrasound images acquired by an ultrasound probe connected to said device, and comprising:
   a first calculator, associated with a first memory, for implementing a classifier configured to classify in real time the ultrasound images received in real time by the device and to associate each image with a class for generating a quality indicator as a function of said associated class;
   a display for, in real time, displaying the received ultrasound images and for displaying the last generated quality indicator;
   a second calculator, associated with a second memory, and configured to perform the following steps of:
      when a sequence of a predefined number of received images includes a rate of images associated with a same class greater than a predefined rate, automatically recording said sequence of images in a third memory; and generating and displaying, on the display in real time, a time indicator representing a number of remaining images to be received to reach said sequence of a predefined number of received images including a rate of images associated with a same class greater than a predefined rate.

2. The device according to claim 1, wherein the classifier is configured to classify an image from among:

a plurality of classes, each representing a particular view of the heart organ; and at least one class representing a view of insufficient quality.

3. The device according to claim 2, wherein the classifier is implemented by a learning function configured from supervised machine learning.

4. The device according to claim 3, wherein the classifier is implemented by a neural network trained by a series of labelled ultrasound images of the heart, the labelled ultrasound images being labelled with labels, said labels including characteristic information of:

a shot of an image of an organ including a characteristic angle of view and/or size;

an image quality; and the presence of a portion of an image of the heart; and/or the presence of a measurable anatomical shape contour.

5. The device according to claim 1, wherein the last generated quality indicator displayed by the display comprises a colored indicator whose color depends on the associated class.

6. The device according to claim 5, wherein at least one of the dimensions of the colored indicator depends on said confidence value.

7. The device according to claim 1, wherein the last generated quality indicator displayed by the display comprises a gauge whose filling depends on the value of the time indicator.

8. A system comprising a device according to claim 1 and an ultrasound probe adapted to be connected to said device so as to transmit ultrasound images captured by the ultrasound probe to the device.

9. A method for assisting in generating a computer-implemented sequence of ultrasound images, the method comprising:

receiving and continuously displaying ultrasound images from an ultrasound probe;

classifying in real time the ultrasound images that have been received, and associating each image with a class;

generating and displaying a quality indicator as a function of said class associated with the classified ultrasound image;

when a sequence of a predefined number of received images includes a rate of images associated with a same class greater than a predefined rate, automatically recording said sequence of images in a memory, and generating and displaying in real time a time indicator representing the number of remaining images to be received to reach said sequence of a predefined number of received images including a rate of images associated with a same class greater than a predefined rate.

10. The method according to claim 9, wherein a predefined fraction of the received images are classified, said predefined fraction being controllable by a user interface.

11. The method according to claim 9, wherein the method further comprises selecting a first class representing a particular first view of the heart, said selection automatically generating:

displaying a first pre-recorded image corresponding to an image of the first ultrasound view of the heart of said first selected class, and/or displaying a first pre-recorded setpoint of ultrasound probe position on a patient to capture said first particular view of the heart.

12. A computer program product comprising instructions that cause a device to perform the steps of the method according to claim 9.

13. A non-transitory computer readable support, on which the computer program according to claim 12 is recorded.

* * * * *